United States Patent [19]

Kraus et al.

[11] Patent Number: 5,718,680
[45] Date of Patent: Feb. 17, 1998

[54] CATHETER SYSTEM WITH PUSH ROD FOR ADVANCEMENT OF BALLOON ALONG GUIDEWIRE

[75] Inventors: Jeff L. Kraus; Michael J. Horzewski, both of San Jose, Calif.

[73] Assignee: Danforth Biomedical Incorporated, Menlo Park, Calif.

[21] Appl. No.: 700,939

[22] Filed: Aug. 21, 1996

Related U.S. Application Data

[62] Division of Ser. No. 277,878, Jul. 20, 1994, Pat. No. 5,578,009.

[51] Int. Cl.$^6$ .................................................. A61M 31/00
[52] U.S. Cl. .......................... 604/53; 604/96; 604/164; 606/194; 128/898
[58] Field of Search .................... 604/96, 102, 166, 604/169, 264, 280, 49, 52, 53; 606/191–195, 198; 128/772, 898

[56] References Cited

U.S. PATENT DOCUMENTS

| | | | |
|---|---|---|---|
| 4,517,979 | 5/1985 | Pecenka | 606/195 X |
| 4,545,367 | 10/1985 | Tucci | 606/195 X |
| 4,771,777 | 9/1988 | Horzewski et al. | 604/102 X |
| 4,988,356 | 1/1991 | Crittenden et al. | 606/192 |
| 5,002,556 | 3/1991 | Ishida et al. | 606/191 |
| 5,024,658 | 6/1991 | Kozlov et al. | 604/96 |
| 5,171,222 | 12/1992 | Euteneuer et al. | 604/102 |
| 5,181,921 | 1/1993 | Makita et al. | 606/195 |
| 5,205,822 | 4/1993 | Johnson et al. | 604/96 |
| 5,222,970 | 6/1993 | Reeves | 606/195 |
| 5,267,958 | 12/1993 | Buchbinder et al. | 604/96 |
| 5,425,714 | 6/1995 | Johnson et al. | 604/102 |
| 5,439,445 | 8/1995 | Kontos | 604/96 |
| 5,536,250 | 7/1996 | Klein et al. | 604/96 |
| 5,578,009 | 11/1996 | Kraus | 604/96 |
| 5,591,194 | 1/1997 | Berthiaume | 606/192 |

*Primary Examiner*—Michael Powell Buiz
*Assistant Examiner*—Chalin Smith
*Attorney, Agent, or Firm*—Townsend and Townsend and Crew LLP

[57] ABSTRACT

An elongated rod terminating in an abutment device with a lumen for passage of a guidewire is used to push an angioplasty balloon along the guidewire and through a vasculature to a location where treatment is needed. The balloon is fed by an inflation tube which remains independent of the guidewire and need not have axial rigidity. This combination of components permits one to exchange balloons without the need for a guidewire extending 100 cm or more outside the patient's body. Guidewire exchanges are also possible in cetain embodiments of the concept, and possibilities for perfusion are also presented. The guidewire passes through a tube inside the balloon which can also be used for perfusion of the patient's blood when the guidewire is withdrawn.

8 Claims, 6 Drawing Sheets

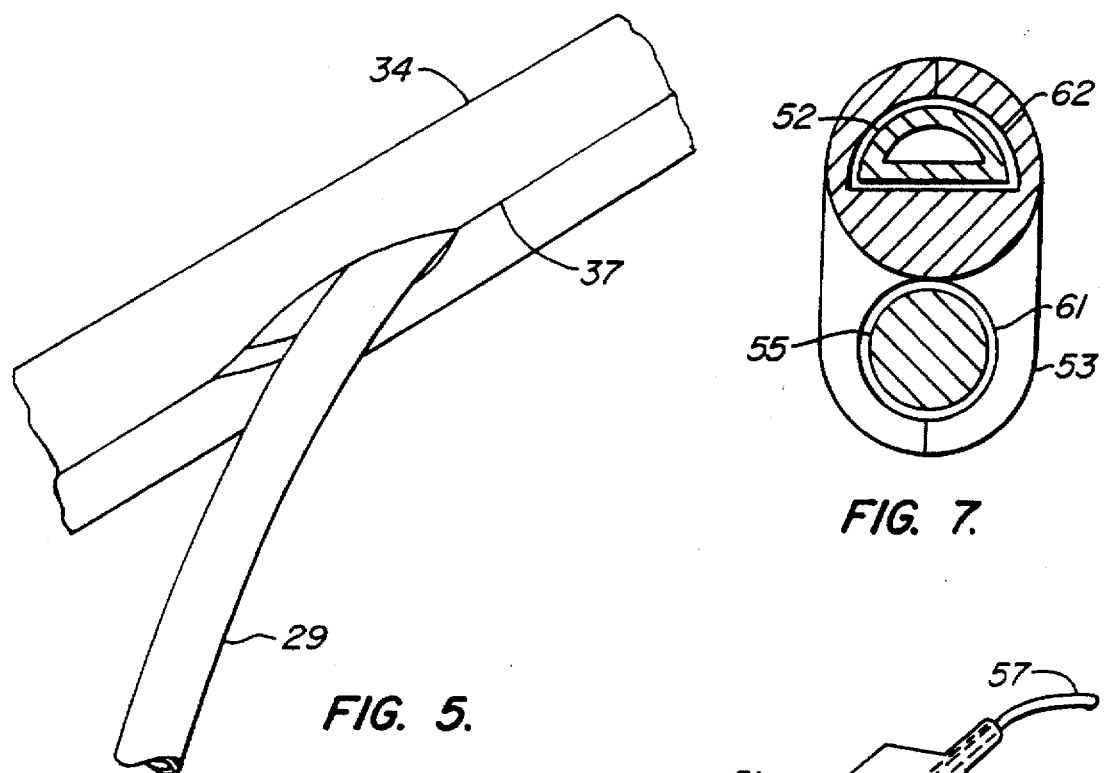
FIG. 5.
FIG. 7.
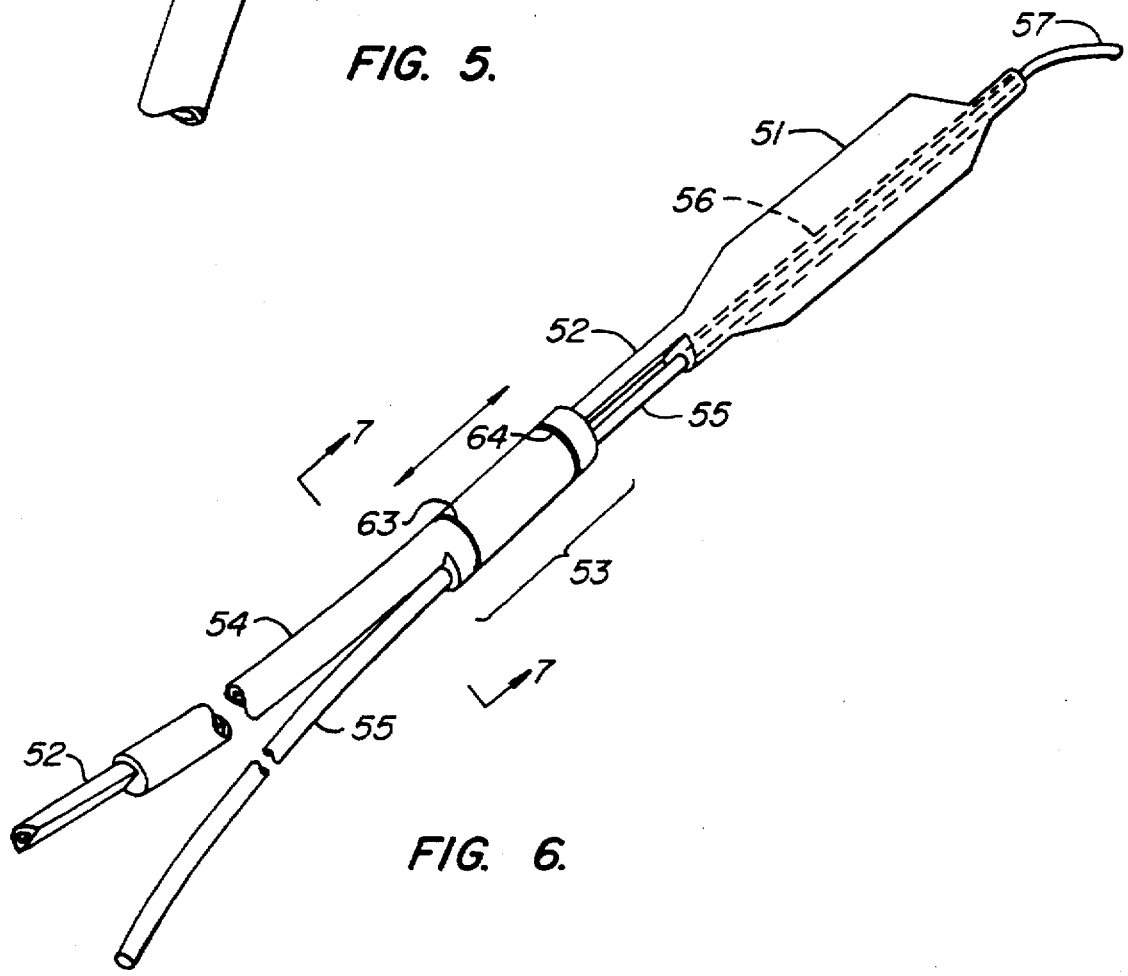
FIG. 6.

CATHETER SYSTEM WITH PUSH ROD FOR ADVANCEMENT OF BALLOON ALONG GUIDEWIRE

This is a Division of application Ser. No. 08/277,878 filed Jul. 20, 1994, now U.S. Pat. No. 5,578,009.

This invention resides in the field of angioplasty, and relates in particular to catheters and catheter components used in performing angioplasty procedures.

BACKGROUND OF THE INVENTION

Angioplasty is a procedure widely used for the treatment of blocked arteries and has been developed to the point where it is effective for blockages varying considerably in density, size and location in the vasculature, and has also been used in combination with other procedures. With such a wide scope of applicability, a considerable amount of variation can be encountered in terms of the therapeutic needs for treating a blockage and any conditions associated with it, as well as the means of meeting those needs. For example, the ease of placing the balloon tip of the catheter at the desired location, the size and type of balloon needed, the need for other means of ablating the blockage or otherwise treating the vessel, can all vary widely, and it is frequently impossible to accurately predict each of these in advance of the procedure. As a result, the physician must often exchange a guidewire or balloon after it has been inserted.

Over-the-wire catheters are designed to permit these types of exchanges. Due to the distance that the catheter must be inserted inside the body to reach the site where treatment is to be performed, however, these catheters are generally about 135 cm or more in length. While drawing the catheter backward over the guidewire, of course, the physician must maintain a grip on the guidewire to hold its position. As a result, the guidewire will generally be at least twice as long as the catheter. Alternatively, a guidewire of shorter length, but one to which an extension can be attached, will be used. In either case, the procedure is awkward, the extra length or the extension interfering with the ease and speed of the exchange and of the procedure as a whole.

SUMMARY OF THE INVENTION

This invention resides in a balloon-tipped catheter system for angioplasty procedures which permits exchange of a balloon without removal of the guidewire and without requiring a guidewire of double or otherwise extraordinary length. With its unusual construction, the system also permits perfusion of blood through an angioplasty balloon from surrounding regions immediately adjacent to the balloon ends independently of whether the balloon is inflated.

The system consists of a combination of components, the primary components being:

(a) a guidewire;

(b) a balloon with a supply or inflation tube for inflation purposes and a through-passage, separate from the inflation tube, for the guidewire; and (c) an elongated rod terminating in a sliding device to travel along either the guidewire, the inflation tube or both to abut the proximal end of the balloon or the proximal end of any short tubular extension at the proximal end of the balloon, the rod having sufficient axial rigidity that it can advance the sliding device through the vasculature to push the balloon along the guidewire.

The balloon will thus be inserted into the vasculature and advanced over the guidewire toward the point of the blockage by the sliding device which is in turn manipulated from outside the body by the elongated rod. When an exchange is needed, the balloon will be removed by pulling the inflation tube to draw the balloon back over the guidewire. The separation of the guidewire from the balloon inflation tube permits the two to be held separately outside the patient's body so that the guidewire can be gripped at a point close to the point of entry into the body while the balloon is being withdrawn. The rod which supports the sliding device is likewise independent of the guidewire outside the body. This allows the physician to advance the balloon the full distance of the guidewire while again gripping the guidewire close to its point of entry in the body. Since it can be held so close to the point of entry, the guidewire therefore need be only slightly longer than the length it penetrates the vasculature. In addition, the shaft profiles of the guidewire, the balloon inflation tube, and the push rod, can all be very small while still providing lumens of adequate size for inflation of the balloon and for the guidewire.

Embodiments of the invention in which only the guidewire passes through the sliding device are fully sufficient for procedures in which the balloon may be exchanged without disturbing the guidewire. In variations of these embodiments, the sliding device contains two lumens and the supporting rod contains a lumen as well. One lumen of the sliding device is specially configured to be advanced over the inflation line while the other lumen is a continuation of the supporting rod lumen. This enables a guidewire to be passed through the supporting rod and sliding device into the balloon through-passage. Longitudinal slits in both the inflation line lumen and the supporting rod lumen then permit the guidewire to be separated from the rod outside the patient's body, and detached from the inflation line, once again permitting the guidewire to be gripped close to the body.

Blood perfusion through the balloon, when desired, is achieved by simply withdrawing the guidewire from the balloon a sufficient distance to clear the opening to the guidewire through-passage at the proximal end of the balloon. Blood then flows through the open through-passage, entering the passage at one end of the balloon and leaving it at the other. This provides a short perfusion path which is at most slightly longer than the length of the balloon.

These and other features and advantages of the invention will be apparent from the description which follows.

BRIEF DESCRIPTION OF THE DRAWINGS

FIG. 5 is an enlarged detail view of two of the components of the embodiment of FIGS. 3 and 4.

FIG. 6 is a perspective view of components of a third embodiment of the invention.

FIG. 7 is a cross section taken along the line 7—7 of FIG. 6.

DETAILED DESCRIPTION OF THE INVENTION AND PREFERRED EMBODIMENTS

While this invention is generic in scope, it will be best understood by a detailed discussion of specific embodiments.

Figure 1:
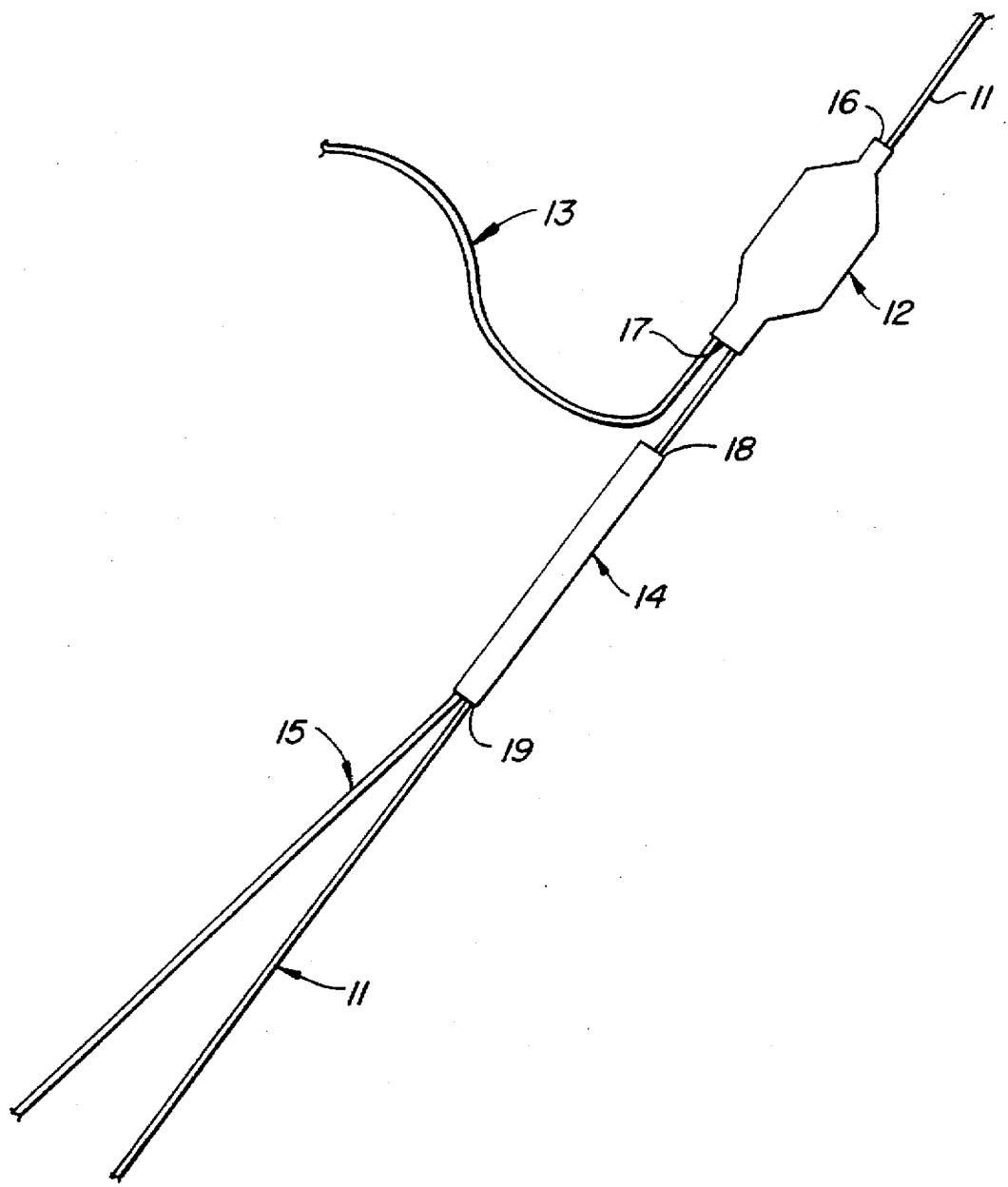
FIG. 1 is a planar view of the components of one embodiment of the invention.

FIG. 1 depicts portions of the three primary components of one system in accordance with the invention. The components are a guidewire 11, an inflatable angioplasty balloon 12 joined to flexible tubing 13 serving as an inflation/deflation line, and a sliding device 14 (referred to herein for convenience as a "bumper") joined to the distal end of a elongated supporting rod 15 (referred to herein for convenience as a "push rod"). The distal end of the guidewire is toward the upper right corner of the Figure. Accordingly, the balloon 12 has a distal end 16 and a proximal end 17, and the inflation/deflation line 13 feeds the balloon at the proximal end 17 of the balloon. The bumper 14 in this embodiment is in the form of a cylinder with a distal end 18 and a proximal end 19, the distal end 18 of the cylinder abutting the proximal end 17 of the balloon when the bumper is advanced, and the push rod 15 joined to the bumper at its proximal end 19.

The bumper 14 in this embodiment contains a single lumen extending through it in the longitudinal direction to permit passage of the guidewire 11. The lumen provides sufficient clearance to permit the bumper to be slid easily over the guidewire. The push rod 15, like the guidewire itself, is flexible enough to permit it to conform to the curves and directional changes encountered in the vasculature yet with sufficient axial rigidity (or to use a term which is commonly used in this art, "pushability") to allow it to be advanced forward from outside the body without kinking or bending back over itself.

Figure 2:
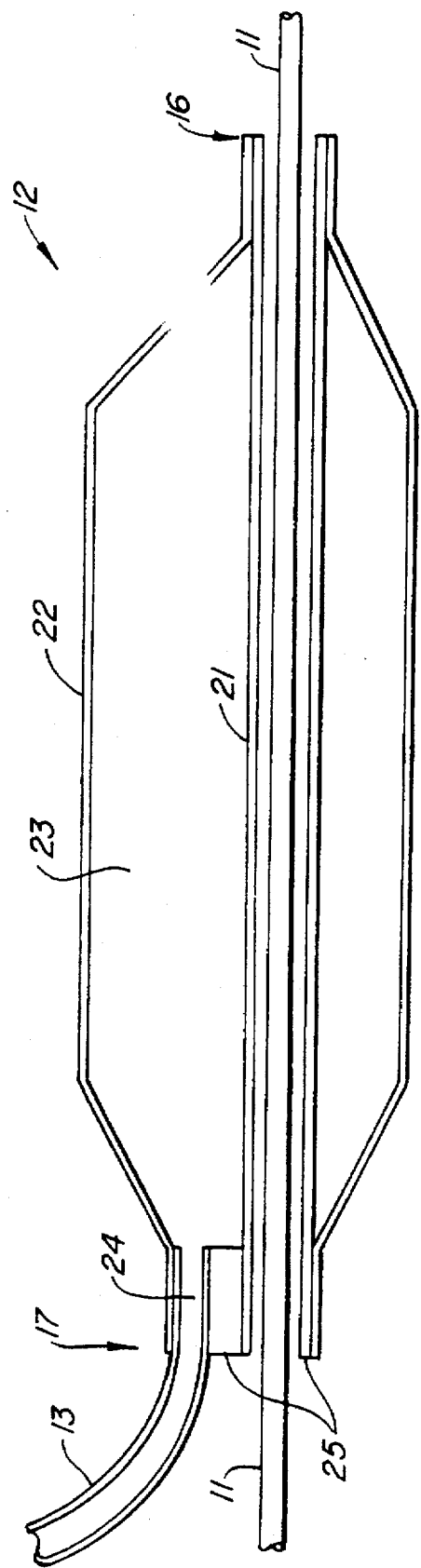
FIG. 2 is a longitudinal cross section of the balloon component of FIG. 1.

The interior of the balloon is shown in the cross section view of FIG. 2, in which the distal end 16 of the balloon is at the right side and the proximal end 17 is at the left. The balloon contains an internal tubular member 21 which spans the balloon interior from the proximal end to the distal end and provides a through-passage for the guidewire 11. The tubular member 21 is also sufficiently stiff to maintain axial elongation of the balloon, i.e., to prevent the balloon from collapsing back along its longitudinal axis as the balloon is being pushed from its proximal end 17 through the vasculature and particularly through an arterial blockage where high resistance may be encountered.

The sheath 22 of the balloon is sealed around both ends of the internal tubular member 21 to form an inflatable cavity 23 which encircles the tubular member. This inflatable cavity 23 is fed by the inflation/deflation line 13 at a port 24 which is adjacent to the internal tubular member 21. The inflation/deflation port 24 is offset from the internal tubular member 21 to leave sufficient area 25 at the proximal end of the balloon surrounding the opening of the tubular member for contact by the distal end 18 of the bumper (FIG. 1) without interfering with or damaging the inflation/deflation line 13. alternatively, the inner tubular member 21 may be connected to a multilumen fitting at the proximal end of the balloon to form a similar configuration.

Figure 3:
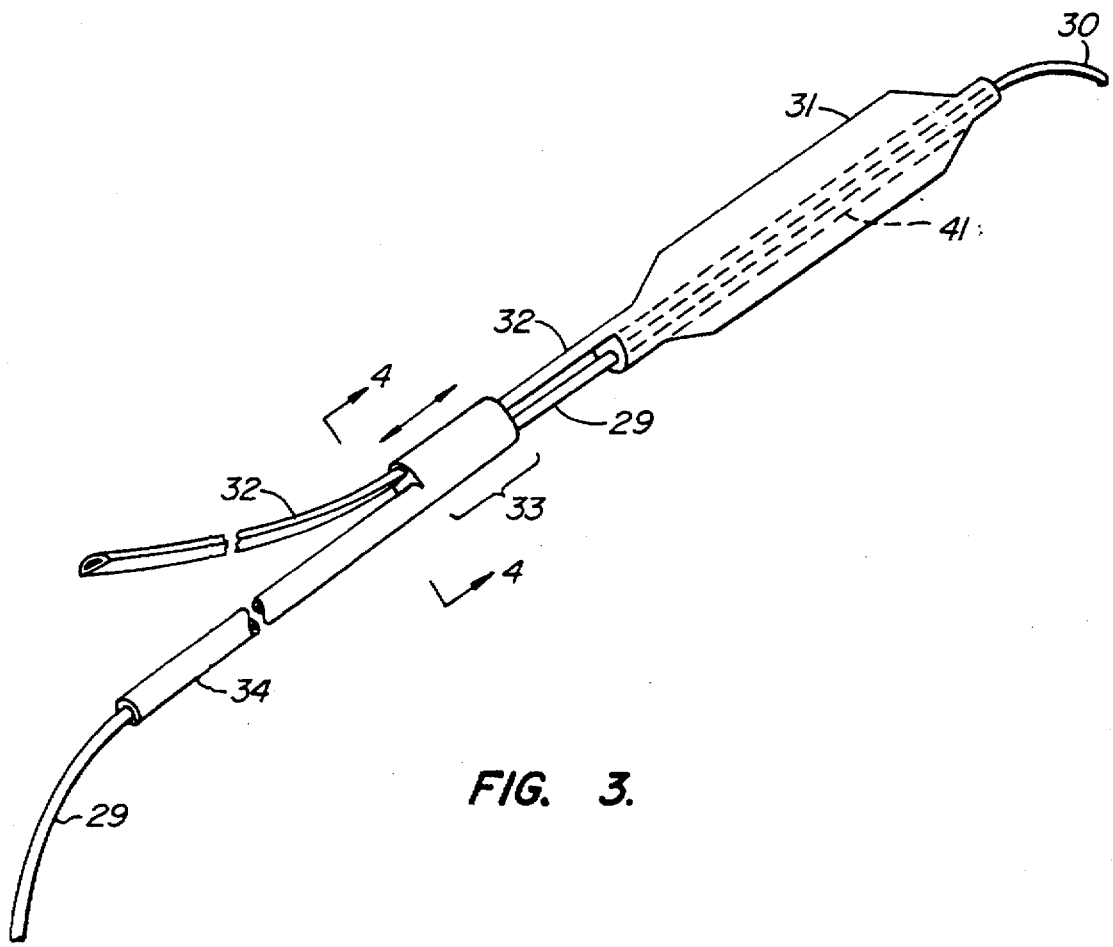
FIG. 3 is a perspective view of components of a second embodiment of the invention.
Figure 4:
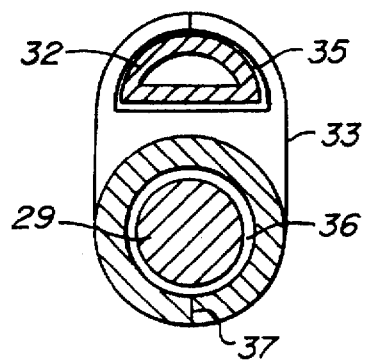
FIG. 4 is a cross section taken along the line 4—4 of FIG. 3.

A further structure within the scope of this invention is shown in FIGS. 3, 4 and 5. The components of this structure are designed to permit exchange of one guidewire for another without removal of the balloon, and also to permit perfusion of a functional fluid through the balloon to the region of the vasculature at the distal end of the balloon, by removing the guidewire and perfusing the fluid through the guidewire lumen. The components shown in FIG. 3 include a balloon 31 with an inflation/deflation line 32 leading to the inflatable cavity inside the balloon, a bumper 33 at the distal end of a push rod 34, and a guidewire 29 passing through the push rod, the bumper and the balloon, with the distal tip 31 of the guidewire emerging from the distal end of the balloon. These components have the same characteristics as the similarly-named components in the embodiment shown in FIG. 1.

FIG. 4 is a cross section taken at the line 4—4 of FIG. 3, and FIG. 5 is an enlarged segment view of the guidewire 29 and the push rod 34.

As seen in FIG. 4, the bumper 33 contains a lumen 35 as in the embodiment of FIG. 1, except that the lumen in this case is designed for passage of the inflation/deflation line 32 rather than the guidewire. Like the lumen in the bumper of FIG. 1, the inflation/deflation line lumen 35 of FIGS. 3 and 4 extends only through the bumper itself.

A second lumen 36 extends through both the bumper 33 and the push rod 34. This lumen is used for passage of the guidewire. This guidewire lumen 36 contains a longitudinal slit 37 through which the guidewire can be removed or inserted. The slit 37 is shown in an open condition in FIG. 5. The material from which the push rod 34 is made is sufficiently resilient to permit the slit to be stretched open but to close the slit once the stretching force is removed. The slit 37 may extend the full combined length of the push rod 34 and the bumper 33. Alternatively, the slit may extend only the length of the push rod and either not extend into the bumper or only partially so.

The balloon 31 is similar to the balloon of the embodiment of FIG. 1, with an identical internal tubular member 41 (shown in dashed lines in FIG. 3) to maintain elongation of the balloon and to provide a through-passage for the guidewire, and the same relative positions of the proximal opening 38 of the tubular member and the point of entry of the inflation/deflation lumen 32. When the guidewire is in place, it thus passes through the guidewire lumen 36 in the push rod and the internal tubular member 41 in the balloon.

As seen in FIG. 4, the shorter lumen 35 for the inflation/deflation line 32, and the inflation/deflation line itself have specially shaped cross sections to prevent the rotation of one relative to the other and to thereby maintain alignment between the guidewire lumen 36 in the push rod and the internal tubular member in the balloon. The cross sections shown in the drawing are D-shaped. Any non-circular shape will suffice, however.

The components of the system shown in FIGS. 3, 4 and 5 may be used in a variety of procedures. For example, the balloon 31 and the bumper 33 can be assembled outside the patient's body by threading the inflation/deflation line 32 backwards through the short bumper lumen 35. The guidewire is then inserted into the vasculature past the region where treatment is desired, using conventional techniques of guidewire placement, and the combined balloon and bumper are then threaded over the guidewire and advanced into the vasculature by the push rod 34. The operator can maintain a grip on the proximal end of the guidewire by forcing the push rod slit laterally over the guidewire in stages at a point distal to the operator's grip but still outside the patient's body.

If it is then necessary to exchange the balloon, this is done without removal of the guidewire, by pulling on the inflation/deflation line 32 to withdraw the balloon while also pulling on the push rod 34 to withdraw the push rod and bumper 33. Withdrawing the balloon by this procedure is the same as withdrawing the balloon in the assembly shown in FIG. 1, since the inflation/deflation line is separated from and independent of the guidewire. Withdrawing the push rod 34 without withdrawing the guidewire, however, and without requiring a second length of guidewire extending outside the patient's body, is accomplished by laterally pulling the push rod away from (i.e., off of) the guidewire at a point close to the point of entry into the body, as shown in FIG. 5. The guidewire thus passes through the slit 37 in the push rod to separate it from the push rod. In this manner, the operator can maintain a grip on the guidewire close to the patient's body as in the embodiment of FIG. 1. Once the balloon and the bumper are disengaged entirely from the guidewire, a new balloon can be assembled to the bumper in the same manner as the first balloon, and then advanced along the guidewire, again in the same manner.

Exchange of the guidewire without removal of the balloon can also be accomplished, simply by removing the existing guidewire through the guidewire lumen 35 without removing the push rod 34 and without the need for passing the guidewire through the slit 37, and replacing the withdrawn guidewire with a new guidewire. The guidewire lumen 35 in the push rod and the internal tubular member opening 38 are held in alignment during this procedure by the fixed orientation of the push rod relative to the balloon, which is in turn maintained by the complementary non-circular cross sections of the bumper lumen 35 and the inflation/deflation the 32.

The components as shown may also be used for perfusion of a region of the vasculature with a functional fluid from outside the patient's body. The functional fluid may for example be a drug or a solution of a contrast agent for imaging purposes, and will pass through the vasculature and out the distal end of the balloon. The guidewire lumen may be used as a perfusion lumen. This is easily done by withdrawing the guidewire, leaving the balloon and push rod in place. The guidewire lumen 36 and the internal tubular member in the balloon are then available for the passage of the perfusion fluid. Alignment of these passages is maintained by the non-circular cross sections as indicated above. In addition, the contact surfaces at the distal end 39 of the bumper and the proximal end 40 of the balloon surrounding the internal tubular member opening 38 are both flat, to provide full contact around the circumference of the passage and minimal opportunity for leakage outward in the lateral direction.

A third variation on the structures discussed above is that shown in FIGS. 6 and 7. The components of this structure include a balloon 51, an inflation/deflation line 52 leading to the cavity inside the balloon, a bumper 53 at the distal end of a push rod 54, and a guidewire 55 passing through the bumper 53 and an internal tubular member 56, with the distal end 57 of the guidewire protruding from the distal end of the balloon 51. In this structure as in the structure of FIG. 3, there are two lumens through the bumper, one 61 extending only through the bumper itself and the other 62 extending through both the bumper and the push rod. This structure differs, however, in that the inflation/deflation line 52 of noncircular cross-section passes through the lumen 62 which extends the length of the push rod, and the circular cross-section guidewire 55 passes through the lumen 61 which extends only through the bumper. The lumen 62 through the push rod is of a non-circular cross section to match that of the inflation/deflation line 52.

Figure 8:
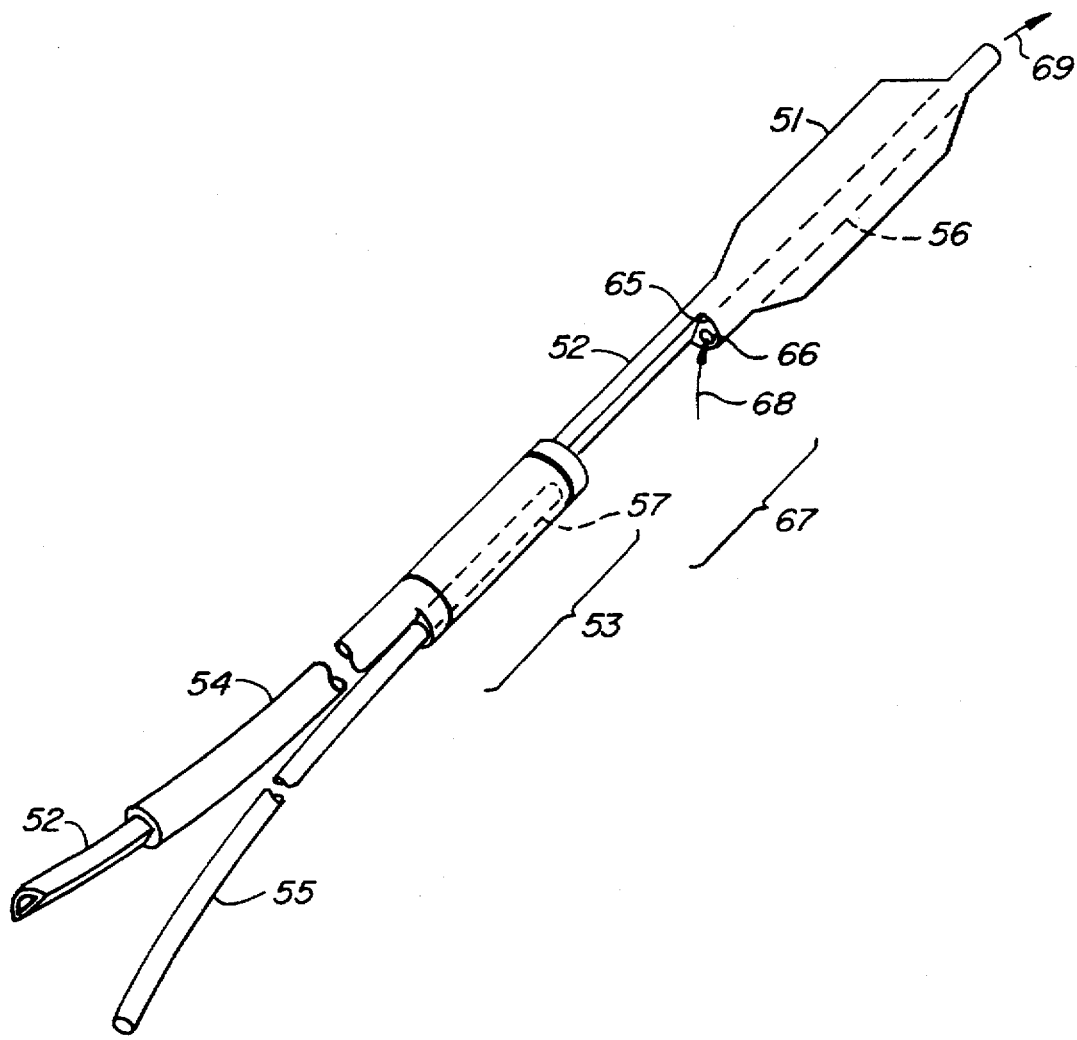
FIG. 8 is another perspective view of the embodiment shown in FIG. 6, but with the guidewire retracted.

The use of the system of FIGS. 6 and 7 is similar to that of the system of FIGS. 3, 4 and 5 for advancing a balloon along a guidewire and removing a balloon and replacing it with another balloon, without the need for a long guidewire. The structure of FIGS. 6 and 7 is not suitable for guidewire exchange without removing the push rod and bumper. It is particularly well adapted, however, for permitting passage of blood across the region of treatment during an angioplasty procedure. This is accomplished, as shown in FIG. 8, by withdrawing the bumper 53 a short distance to expose the proximal end 65 of the balloon, and withdrawing the guidewire 55 far enough to clear the internal tubular member 56 entirely and thereby permit the surrounding blood free access to the internal tubular member through the opening 66 at the proximal end of the tubular member.

The gap 67 between the distal end of the bumper 53 and the proximal opening 66 of the tubular member is not critical and may be less than 15 cm. The guidewire may be withdrawn to the point that its distal end 57 is inside the bumper. This is preferred for a guidewire with a curved tip if the guidewire is to be eventually reinserted through the balloon. For angioplasty procedures where a guide catheter surrounding the functional catheter is used, the bumper 53 and guidewire tip 57 are preferably withdrawn to a position just inside the guide catheter. Radiopaque marker bands 63, 64 aid in the visualization of the position of the bumper during its withdrawal. In any event, with the internal tubular member 56 open and its proximal opening 66 exposed, the patient's blood can enter the tubular member at the proximal opening, pass through the tubular member, and leave to reenter the blood stream at the distal end of the balloon. The path of blood flow is indicated by the arrows 68, 69.

Figure 9:
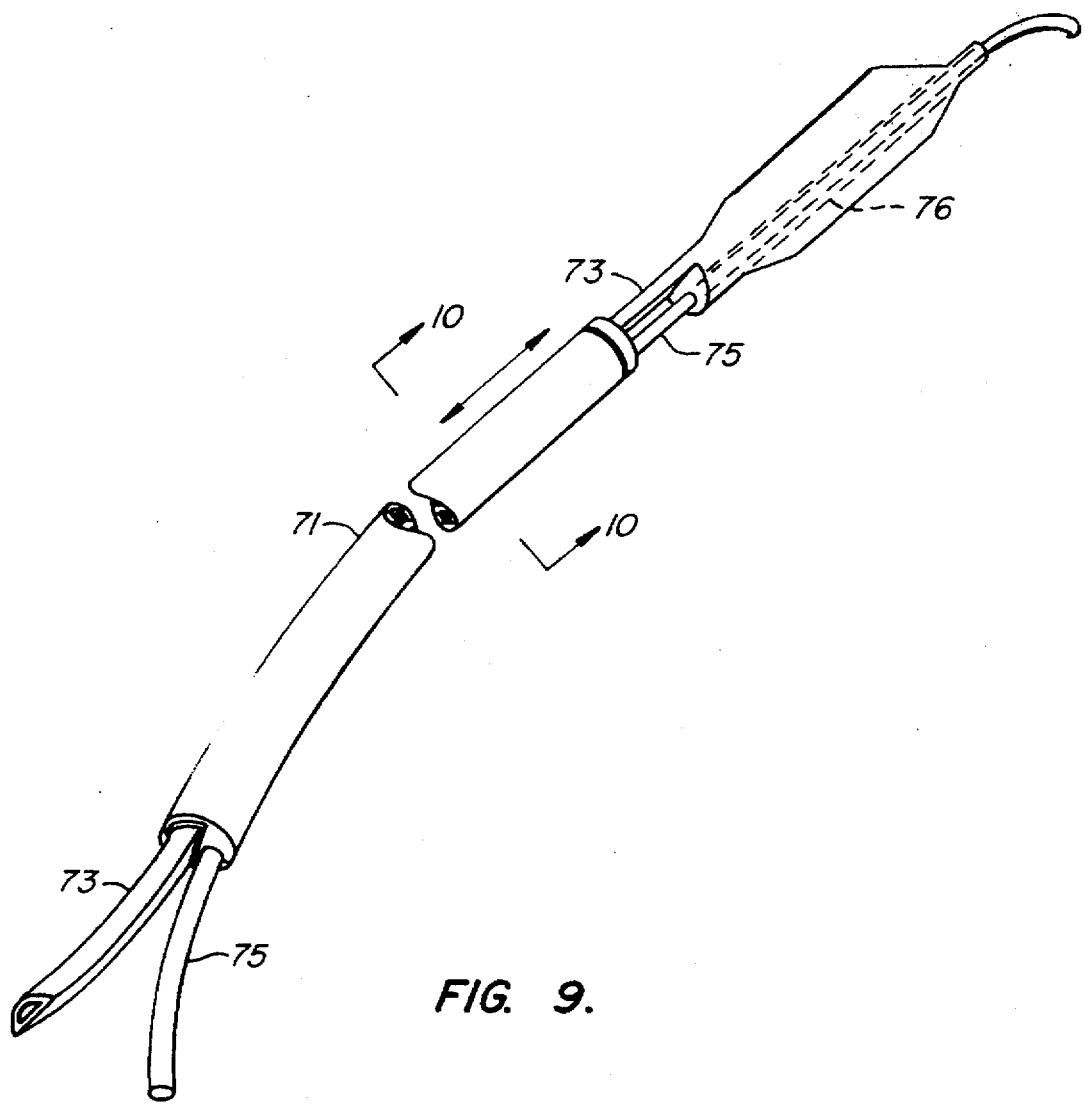
FIG. 9 is a perspective view of components of a third embodiment of the invention.
Figure 10:
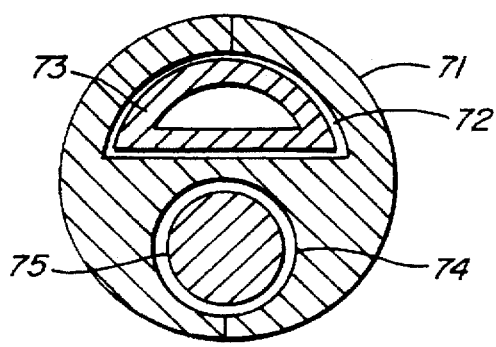
FIG. 10 is a cross section taken along the line 10—10 of FIG. 9.

A fourth variation is shown in FIGS. 9 and 10. Here the bumper and the pushrod are combined to form a single continuous dual-lumen rod 71, with a radiopaque marker band 77 at its distal tip. One of the two lumens 72 receives the inflation/deflation line 73, and both this lumen and the inflation/deflation line are of a non-circular cross section. The other lumen 74 receives the guidewire 75. Both the rod 71 and the guidewire 75 may be withdrawn a short distance to expose the internal tubular member 76 of the balloon for blood perfusion, as in the system of FIGS. 7 and 8. In this system, however, both lumens 72, 74 are of sufficient length to extend outside the patient's body while the balloon remains fully inserted. This permits the operator to perform a guidewire exchange without removing the balloon, simply by leaving the rod 71 in place (abutting the proximal end of the balloon, rather than separated from the balloon by as small gap as shown in FIG. 9), withdrawing the guidewire through the rod, and inserting the new guidewire back through the rod in place of the first guidewire.

The components in these various embodiments of the invention may be made of a variety of materials, as are the components of catheters and guidewires of the prior art. Likewise, the dimensions of the various components may vary, and are not strictly critical to the invention. In most applications, the bumper will be a cylinder of from about 0.5 cm to about 35 cm in length, and preferably from about 15 cm to about 30 cm in length. Likewise, the balloon, including its proximal and distal extremities, will generally be less than about 6 cm in length, and most often from about 3 cm to about 6 cm in length, the non-tapering central portion of the balloon being from about 2 cm to about 4 cm in length. The length of the push rod will most often be at least about 100 cm, and preferably at least about 120 cm.

The materials of construction may vary widely, and materials conventionally used or known or disclosed for use in catheters may be used here as well. Prime examples of materials for the various components are high density polyethylene, polyurethane, polyimide, hypotube (alloys of stainless steel or nickel and titanium), polytetrafluoroethylene and related materials known as Teflon, and composites of these materials, although any readily formable or extrudable material from which a shaft with dimensions and lumens of the requisite precision can be made may be used.

As one example of a typical construction for the components shown in FIG. 1, the balloon may be a polyethylene balloon 3.0 mm in expanded diameter, the inflation/deflation line may be polyimide with an internal diameter of 0.016 inch (0.041 cm) and an outer diameter of 0.018 inch (0.046 cm), the push rod may be steel coated with Teflon (polytetrafluoroethylene) with a diameter of 0.017 inch (0.043 cm), the bumper may be 25 cm in length with a guidewire lumen of 0.014 inch (0.036 cm) in diameter.

The foregoing is offered primarily for purposes of illustration. It will be readily apparent to those skilled in the art that the materials, dimensions, procedural steps and other parameters of the system described herein may be further modified or substituted in various ways without departing from the spirit and scope of the invention.

What is claimed is:

1. A method of placing an angioplasty balloon at a selected location in a vasculature, said method comprising:

(a) advancing a guidewire through said vasculature until the distal tip of said guidewire is at least as far into said vasculature as said selected location, leaving a proximal segment of said guidewire outside said vasculature;

(b) placing an angioplasty balloon onto said guidewire, said angioplasty balloon having an inflatable cavity fed by an external tubular member and containing an internal tubular member forming an axial through-passage that is independent of said inflatable cavity, by placing said axial through-passage over said proximal segment;

(c) placing an abutment means onto said proximal segment proximal to said angioplasty balloon, said abutment means adapted to abut the proximal end of said balloon and to slide along said guidewire; and (d) pushing said abutment means along said guidewire, thereby advancing said angioplasty balloon to said selected location.

2. A method in accordance with claim 1 in which said angioplasty balloon is a maximum of about 6 cm in length.

3. A method in accordance with claim 1 in which said abutment means comprises a cylinder of from about 0.5 cm to about 35 cm in length with a lumen extending therethrough to receive said guidewire, and an elongate rod.

4. A method in accordance with claim 3 in which said cylinder contains a slit running the length of said lumen, and step (c) comprises inserting said proximal segment of said guidewire through said slit.

5. A method for placing an angioplasty balloon and guidewire into a vasculature and exchanging said guidewires without removing said angioplasty balloon from said vasculature, said method comprising:

(a) advancing a first guidewire into said vasculature;

(b) placing an angioplasty balloon having an axial through-passage and an elongated inflation tube which is not in communication with said through-passage onto said first guidewire by placing said through-passage over the proximal end of said first guidewire and pushing said angioplasty balloon along said first guidewire with an elongated abutment rod, with said first guidewire passing through a lumen extending the length of said abutment rod, said abutment rod configured to maintain alignment of said lumen with said through-passage;

(b) withdrawing said first guidewire from said angioplasty balloon and said abutment rod while retaining said angioplasty balloon and said abutment rod in said vasculature; and (c) inserting a second guidewire into said vasculature through said lumen in said abutment rod and through said through-passage in said angioplasty balloon.

6. A method of performing angioplasty on a region of treatment in a vasculature while permitting the passage of blood across said region of treatment, said method comprising:

(a) advancing a guidewire through said vasculature until the distal tip of said guidewire passes through said region of treatment;

(b) placing an angioplasty balloon having an axial through-passage and an inflation tube onto said guidewire by inserting a proximal end of said guidewire through said axial through-passage;

(c) advancing said angioplasty balloon over said guidewire to said region of treatment by passing said guidewire through an abutment tube through which said inflation tube also passes and advancing said abutment tube along said guidewire;

(d) when said angioplasty balloon is within said region of treatment, proximally retracting said abutment tube over said inflation tube and withdrawing said guidewire from said axial through-passage, thereby opening said through-passage for blood flow; and (e) inflating said angioplasty balloon to treat said stenosis.

7. A method in accordance with claim 6 in which said abutment tube is at least about 100 cm in length, said inflation tube passes through the full length of said abutment tube, and said guidewire passes through a distal end of said abutment tube of less than about 35 cm in length.

8. A method in accordance with claim 6 in which said abutment tube is at least about 100 cm in length, and both said inflation tube and said guidewire pass through the full length of said abutment tube.

* * * * *